United States Patent [19]

Wohl

[11] 4,209,624

[45] Jun. 24, 1980

[54] PROCESS FOR PREPARING SUBSTITUTED BIS(AMIDINOUREAS)

[75] Inventor: Ronald A. Wohl, Morris Plains, N.J.

[73] Assignee: Cooper Laboratories, Inc., Palo Alto, Calif.

[21] Appl. No.: 817,040

[22] Filed: Jul. 19, 1977

Related U.S. Application Data

[63] Continuation-in-part of Ser. No. 735,318, Oct. 26, 1976, abandoned.

[51] Int. Cl.² ........................................... C07D 295/14
[52] U.S. Cl. .............................. 544/400; 260/501.14; 260/553 R; 546/332; 546/246
[58] Field of Search ..................... 260/553 R, 268 R; 544/382, 400; 546/332, 246

[56] References Cited

U.S. PATENT DOCUMENTS

| | | | |
|---|---|---|---|
| 1,737,192 | 11/1929 | Myron Heyn | 260/564 C |
| 3,113,151 | 12/1963 | McKay et al. | |
| 3,657,337 | 4/1972 | Hoyliban et al. | 260/564 F |
| 3,683,023 | 8/1972 | Winter et al. | 260/564 F |
| 3,960,949 | 6/1976 | Ahrens et al. | 260/564 B |
| 4,022,962 | 5/1977 | Diamond | 260/553 R |
| 4,025,652 | 5/1977 | Diamond et al. | 260/553 R |
| 4,110,328 | 8/1978 | Diamond | 260/553 R |

*Primary Examiner*—Jose Tovar
*Attorney, Agent, or Firm*—John J. Kolano; Thomas R. Boland

[57] ABSTRACT

A process is disclosed for preparing substituted bis-(amidinoureas) by reacting a 1-substituted-4-alkyl-4-isothiobiuret with a compound containing two aliphatic amino groups.

13 Claims, No Drawings

PROCESS FOR PREPARING SUBSTITUTED BIS(AMIDINOUREAS)

RELATIONSHIP OF OTHER APPLICATIONS

This application is a continuation-in-part of Applicant's copending application Ser. No. 735,318, filed Oct. 26, 1976, now abandoned.

BACKGROUND OF THE INVENTION:

This invention relates to methods for preparing amidinoureas (also named as carbamylguanidines, carbamoylguanidines, guanylureas or aminoiminomethylureas) and more particularly to processes for preparing bis(amidinoureas) using isothiobiurets as intermediates.

Substituted amidinoureas, i.e., compounds having the formula $$Z-NH-\overset{O}{\overset{\|}{C}}-NH-\overset{NH}{\overset{\|}{C}}-NH-R$$

wherein: Z is an aliphatic, alicyclic or aromatic group and R is hydrogen or an aliphatic group, have been prepared in several ways. These compounds can be prepared, for example, by reacting ioscyanates of the formula $Z-N=C=O$ with substituted guanidines of the formula $$R-NH-\overset{NH}{\overset{\|}{C}}-NH_2$$

under conditions well known to those skilled in the art. Such a process is disclosed in Curd, F. H. S.; Davey, D. G.; and Richardson, D. N.; J. Chem. Soc. 1949, 1732-1738.

A process of this type for the case wherein R=H is disclosed in Walls, U.S. Pat. No. 3,539,616, issued Nov. 10, 1970. Monosubstituted amidinoureas of the formula $$Z-NH-\overset{O}{\overset{\|}{C}}-NH-\overset{NH}{\overset{\|}{C}}-NH_2$$

have been prepared by ammonolysis of substituted 4-alkyl-4-isothiobiurets, as described in British Patent 1,194,835.

Curd, F. H. S.; Davey, D. G.; Richardson, D. N.; and Ashworth R. deB., J. Chem. Soc. 1949, 1739-1745, disclose the reaction of 1-(p-chlorophenyl)-4-methyl-4-isodithiobiuret with isopropylamine neat or in methanol, and the reaction of 1-(p-chlorophenyl)-4-methyl-4-isodithiobiuret with methylamine in methanol. No reactions of isothiobiurets and no reactions using diamines are disclosed. In particular, since Curd, et al, did not consider the synthesis of bis(amidinoureas) starting from aliphatic diamines, this reference contains no disclosure of the problems which arise in the synthesis of bis(amidinoureas) and no disclosure of the critical properties of the solvent.

Thus, there are no disclosures in the literature which describe the difficulties which arise in synthesizing bis(amidinoureas) having the formula $$Z-NH-\overset{O}{\overset{\|}{C}}-NH-\overset{NH}{\overset{\|}{C}}-NH-Y-NH-\overset{NH}{\overset{\|}{C}}-NH-\overset{O}{\overset{\|}{C}}-NH-Z$$

wherein Z is an aliphatic or alicyclic group and Y is a divalent aliphatic, alicyclic, or heterocyclic radical or combination thereof.

If the reagents and solvents used in synthesizing such bis(amidinoureas) are not carefully chosen the reaction may proceed very slowly or not at all and it may be difficult to isolate the desired product.

SUMMARY OF THE INVENTION

It is an object of this invention to provide a process for synthesizing substituted bis(amidinoureas). A further object is to provide a process for synthesizing such bis(amidinoureas) in good yield. A further object is to synthesize such bis(amidinoureas) by a process which allows them to be easily separated and purified. A further object is to provide a process specially adapted to synthesizing bis(amidinoureas) of the formula:

$$Z-NH-\overset{O}{\overset{\|}{C}}-NH-\overset{NH}{\overset{\|}{C}}-NR-Y-NR-\overset{NH}{\overset{\|}{C}}-NH-\overset{O}{\overset{\|}{C}}-NH-Z$$

wherein Z is an aliphatic or alicyclic group and Y is a divalent organic radical selected from the group consisting of
(1) divalent straight and branched chain aliphatic radicals;
(2) divalent alicyclic and non-aromatic heterocyclic radicals;
(3) divalent carbocyclic aromatic and heterocyclic aromatic radicals having side chains; and
(4) combinations of the above radicals linked directly or through hetero atoms selected from the group consisting of nitrogen, oxygen, or sulfur, and
R is hydrogen or a lower alkyl group.

According to this invention substituted bis(amidinoureas of the formula $$Z-NH-\overset{O}{\overset{\|}{C}}-NH-\overset{NH}{\overset{\|}{C}}-NR-Y-NR-\overset{NH}{\overset{\|}{C}}-NH-\overset{O}{\overset{\|}{C}}-NH-Z$$

where Z is an aliphatic or alicyclic group are prepared by reacting an isothiobirute of the formula $$Z-NH-\overset{O}{\overset{\|}{C}}-NH-\overset{S-R'}{\overset{|}{C}}=NH$$

wherein Z is as defined above, and R' is a lower ($C_{1-4}$) alkyl group, with a compound of the formula RHN-Y-NHR wherein Y is a divalent organic radical selected from the group consisting of
(1) divalent straight and branched chain aliphatic radicals;
(2) divalent alicyclic and non-aromatic heterocyclic radicals;
(3) divalent carbocyclic aromatic and heterocyclic aromatic radicals having side chains; and
(4) combinations of the above radicals linked directly or through hetero atoms selected from the group consisting of nitrogen, oxygen, or sulfur,
R represents hydrogen or a lower alkyl group and RHN— represents an aliphatic amino group. The term "aliphatic amino group" signifies an amino group attached to a saturated carbon atom and having at least one replaceable hydrogen. Thus, primary and secondary aliphatic and alicyclic amines as well as aromatic or heterocyclic compounds having aliphatic amino groups in side chains may be used in the process of this invention.

The solvent for the reaction may be any inert organic solvent, although when the isothiobiuret is reacted in the form of its acid addition salt, a preferred solvent is an organic polar hydroxylic solvent.

The process can be carried out at temperatures between 0° C. and 100° C.

DESCRIPTION OF THE PREFERRED EMBODIMENTS

According to a preferred embodiment of this invention substituted bis(amidinoureas) of the formula

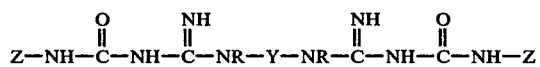

wherein Z, Y, and R are as defined above are prepared by reacting an isothiobiuret acid addition salt of the formula

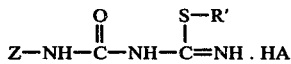

wherein Z is an aliphatic or alicyclic group, R' is a lower ($C_{1-4}$) alkyl group, and A is the anion of acid, with a compound of the formula RHN-Y-NHR wherein Y is a
(1) divalent straight and branched chain aliphatic radicals;
(2) divalent alicyclic and non-aromatic heterocyclic radicals;
(3) divalent carbocyclic aromatic and heterocyclic aromatic radicals having side chains; and
(4) combinations of the above radicals linked directly or through hetero atoms selected from the group consisting of nitrogen, oxygen, or sulfur,
R represents hydrogen or a lower alkyl group and RHN— represents an aliphatic amino group.

The use of the proper solvent is critical for obtaining the advantages of the preferred process. The solvent must be an organic polar hydroxylic solvent. For purposes of this specification "polar solvent" signifies a solvent having a dielectric constant greater than 15. Such solvents include methanol, ethanol, 1-propanol, 2-propanol, 1-butanol, 2-methyl-1-propanol, and 2-butanol.

It is particularly preferred that the organic polar hydroxylic solvent have a dielectric constant greater than 18. Such solvents include methanol, ethanol, 1-propanol, and isopropyl alcohol.

The preferred process can be carried out at temperatures between 0° C. and 100° C., preferably 20° to 85° C.

The Z group in the isothiobiurets used in the process of this invention may be straight or branched chain hydrocarbon groups, saturated carbocyclic rings, or either of these carbon skeletons having substituents which are not incompatible with the isothiobiuret group. Thus, methyl, ethyl, propyl, hexyl, octyl, decyl, 2-ethylhexyl, cyclohexyl, cycloheptyl, cyclohexanemethyl, cyclohexaneethyl, 6-hydroxyhexyl, 6-chlorohexyl, propoxypropyl, and the like are representative Z groups.

The Y groups in the aliphatic diamines of the formula

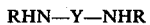

used in the process of this invention include divalent straight and branched chain aliphatic radicals, e.g., 1,4-butanediyl, 1,6-hexanediyl, 1,8-octanediyl, 2-ethyl-1,6-hexanediyl, 2,4-dimethyl-1,6-hexaneediyl, and the like; divalent alicyclic and non-aromatic heterocyclic radicals, e.g., 1,4-cyclohexanediyl, 3,5-piperidinediyl, 2-cyclohexene-1,4-diyl, and the like; divalent carbocyclic aromatic and heterocyclic aromatic radicals having side chains, e.g., 1,4-phenylenebismethyl, 1,4-phenylenebis(2,1-ethanediyl), 2,5-pyridinebis(2,1-ethanediyl), and the like; and combinations of the above radicals linked directly or through hetero atoms selected from the group consisting of nitrogen, oxygen, and sulfur, e.g., 1,4-cyclohexanebis(2,1-ethanediyl), 2,5-piperidinebis(2,1-ethanediyl), 1,4-piperazinebis(2,1-ethanediyl), 1,4-piperazinebis(3,1-propanediyl), 3-methyl-3-aza-1,5-pentanediyl, 1,4,7,10-tetramethyl-1,4,7,10-tetraazadecane, includes terminal NHR group oxybis(3,1-propanediyl), thiobis(3,1-propanediyl) and the like. The amino groups in these compounds must be aliphatic amino groups as defined above.

The Y groups may also generally contain any functional group which is compatible with the isothiobiuret, i.e., does not itself react with the isothiobiuret under the conditions of the reaction.

Specifically included functional groups are tertiary amino groups, secondary amino groups under certain conditions, alcohol groups, ether groups, thioether groups, and carbonyl groups.

The lower alkyl groups suitable for R and R' in the compounds used in the process of this invention include methyl, ethyl, n-propyl, isopropyl, n-butyl, and the like.

It is preferred to carry out the reaction between the isothiobiuret acid addition salt and the compound containing aliphatic amino groups with the reagents dissolved or suspended in methanol, ethanol, or 2-propanol between 20° C. and 85° C. The most preferred solvent is methanol. The reaction is usually complete in a period of time ranging from a few hours to several days. The product may then be isolated by conventional means well known to those skilled in the art.

Since the preferred process is carried out using the 1-substituted-4-alkyl-4-isothiobiuret in the form of an acid addition salt, the corresponding acid addition salt of the amidinourea is obtained. The use of the salt form of the isothiobiuret produces a more rapid reaction, and the salts of the amidinoureas are more easily isolated than the free base forms.

The 1-substituted-4-alkyl-4-isothiobiurets and salts used in the process of this invention may be prepared by any method known in the art. A preferred method is by reacting an isocyanate of the formula Z—N=C=O with an S-alkylisothiourea, preferably S-methylisothiourea in a suitable solvent at a temperature between 0° and 80° C. Suitable solvents for this reaction include water and water-miscible organic solvents such as $C_{1-3}$ alcohols, acetone, tetrahydrofuran, and p-dioxane, alone or in mixtures with water.

1-Substituted-4-alkyl-4-isothiobiurets can also be prepared by other processes, notably by alkylation of thiobiurets, as described, for example in Birthwell, S.; Curd, F. H. S.; Hendry, J. A.; and Rose, F. L., J. Chem.

Soc. (London), 1948, 1645, and Lakra, H. and Dains, F. B., J. Am. Chem. Soc. 51 2220 (1929).

The isothiobiuret salts used in the preferred process of this invention contain one equivalent of acid. That is, one mole of a monobasic acid, one-half mole of a dibasic acid, etc. is used per mole of isothiobiuret. As is well known to those skilled in the art, since isothiobiurets are relatively weak bases it is necessary to use a relatively strong acid to form the acid addition salts. Suitable acids are those having a pKa less than about 5. Thus, mineral acids and the stronger organic acids having a pKa of less than about 5 are useful for preparing the isothiobiuret salts. The suitable acids include hydrochloric acid, hydrobromic acid, hydroiodic acid, sulfuric acid, methanesulfonic acid, acetic acid, and the like.

The preferred process is carried out by reacting two moles the 1-substituted-4-alkyl-4-isothiobiuret salt with a compound containing two aliphatic amino groups. It is preferable when synthesizing bis(amidinoureas) that only two amino groups having replaceable hydrogen be present in the compound containing two aliphatic amino groups. If more than two amino groups having replaceable hydrogen are present, mixtures of products may be obtained.

When the process of this invention is used to prepare bis(amidinoureas) of the formula given above wherein Y contains one or more nitrogen atoms a difficulty is encountered which may be overcome by a particularly preferred embodiment of the process. When two moles of an isothiobiuret salt are reacted with one mole of a compound of the formula

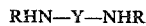

RHN—Y—NHR wherein Y contains one or more nitrogen atoms, the bis(amidinoureas) produced are obtained as mixtures of the diacid salt and salts containing more than two moles of acid. Thus, the empirical formula of the crude product frequently contains 2.3 to 2.5 moles of acid per mole of bis(amidinourea). In purifying the crude material the higher salts are difficult or impossible to recover, and only the salts containing two moles of acid can be isolated. The overall yield is thus less than optimum.

It has now been discovered that yields can be improved and the purification of the product simplified by reacting with the aliphatic diamine a mixture of the isothiobiuret free base and the corresponding isothiobiuret acid addition salt. The proportions of isothiobiuret free base and isothiobiuret acid addition salt in this mixture should be chosen to provide a total amount of isothiobiuret which is equal to or greater than (preferably greater than) the theoretical two equivalents (the stoichiometric amount) but a total amount of acid which is less than the theoretical two equivalents. When the proportions are properly chosen the crude material is essentially the acid addition salt of the bis-(amidinourea) which contains two moles of acid. Under these conditions both the yield of crude product is greater and fewer by-products are produced, so that less of the desired product is lost in the subsequent purification.

The choice of the exact ratios of isothiobiuret free base and isothiobiuret salt to nitrogen-containing aliphatic diamine for optimum yield may vary somewhat depending on the particular aliphatic diamine used in the process. The determination of the optimum ratios in each case is within the competence of one skilled in the art in possession of this disclosure. The ratios will generally lie in the range of 0.05 to 0.7 moles of isothiobiuret (as free base) and 1.4 to 1.95 moles of acid (in the form of the isothiobiuret acid addition salt) per mole of nitrogen-containing aliphatic diamine.

The following examples will illustrate the practice of this invention but are not intended to limit its scope.

EXAMPLE I

This example illustrates the preparation of 1,4-bis[3-(cyclohexanemethylcarbamylguanidino)propyl] piperazine salts by the process of this invention.

A solution of 5.6 g (0.1 mole) of potassium hydroxide in 15 ml of water was introduced into a 250 ml flask equipped with a magnetic stirrer. 13.9 Grams (0.05 mole, 0.1 equivalent) of S-methylisothiuronium sulfate were then added. The suspension was then diluted with 30 ml of tetrahydrofuran.

A solution of 13.9 g (0.1 mole) of cyclohexanemethyl isocyanate in 30 ml of tetrahydrofuran was added dropwise with stirring while the flask was cooled in ice water. The bulk of the tetrahydrofuran was removed on a rotary evaporator. After addition of a small amount of water, the formed oil was extracted from the aqueous phase with several portions of methylene chloride; the combined organic phases were washed with water and dried over anhydrous $K_2CO_3$. Filtration and evaporation yielded 21.6 grams of a slightly turbid oil of 1-cyclohexanemethyl-4-methyl-4-isothiobiuret.

14.3 Grams of this oil were dissolved in 28 ml of isopropyl alcohol, the solution was filtered and acidified with 6.3 ml of concentrated hydrochloric acid while being cooled in an ice bath. A solid precipitate formed. 25 milliliters of diethyl ether were added, and the mixture was stirred and filtered. 6.2 Grams of 1-cyclohexanemethyl-4-methyl-4-isothiobiuret hydrochloride were recovered, M.P. 177°–181° C. M.P. after recrystallization from absolute ethanol 180°–181.5° C.

5.4 Grams (23.5 millimoles) of the above oil of 1-cyclohexanemethyl-4-methyl-4-isothiobiuret were dissolved in 25 ml of isopropyl alcohol and 2.26 g (23.5 millimoles, 1.53 ml) of methanesulfonic acid were added. A thick, white precipitate of 1-cyclohexanemethyl-4-methyl-4-isothiobiuret methanesulfonic acid salt formed which was filtered and washed with a mixture of isopropyl alcohol and diethyl ether. After recrystallization from ethanol the M.P. was 185°–186.5° C.

1.045 Grams (3.93 millimoles of 1-cyclohexanemethyl-4-methyl-4-isothiobiuret hydrochloride and 394 mg (1.97 millimole) of 1,4-bis(3-aminopropyl)piperazine were dissolved in 5 ml of methanol and allowed to stand at room temperature for 7 days. When diethyl ether was added, an oil precipitated which was triturated with ether to yield a hygroscopic crystalline material, 1,4-bis[3-(cyclohexanemethylcarbamylguanidino)-propyl] piperazine di- and tri-hydrochlorides (found 2.5 moles of HCl), M.P. 115°–120° C.

65 Grams (0.2 mole) of 1-cyclohexanemethyl-4-methyl-4-isothiobiuret methanesulfonic acid salt was stirred in 100 ml of methanol to give a suspension. A solution of 20 grams (0.1 mole) of 1,4-bis-(3-aminopropyl)piperazine in 30 ml of methanol was added through an addition funnel. An additional 20 ml of methanol were added through the funnel. The reaction mixture was allowed to stand for five days. The clear solution was then treated with about 1 liter of diethyl ether with stirring. The white precipitate which formed was collected on a filter, washed with diethyl ether, dried, and recrystallized from ethanol to yield 1,4-bis[3-(cyclohexanemethylcarbamylguanidino)propyl] piperazine dimethanesulfonic acid salt, M.P. 178°–180° C.

EXAMPLE II

This example illustrates the preparation of 1,4-bis[3-(tert-octylcarbamylguanidino)propyl] piperazine by the process of this invntion.

15.3 Grams (0.07 mole) of S-methylisothiuronium iodide were dissolved in 75 ml of anhydrous acetone and 11 ml of triethylamine were added, while the solution was cooled in an ice bath. 10.87 Grams (0.07 moles) of tert-octyl isocyanate dissolved in 10 ml of acetone were added dropwise over a period of about 5 minutes. A precipiate formed at once. The mixture was stirred for 3½ hours. The precipitate was filtered off and the filtrate was treated with water and allowed to stand overnight in a refrigerator. The gum which formed was separated from the water by decantation, and dissolved in diethyl ether. The solution was extracted with water and the ether was stripped at room temperature to yield 15.3 grams of a clear oil. 7 Grams of this oil was dissolved in 30 ml of isopropyl alcohol and 2.9 ml of concentrated hydrochloric acid was added dropwise. The resulting suspension was treated with 15 ml of diethyl ether and the white precipitate was collected on a filter and recrystallized from isopropyl alcohol to yield 3.8 grams of 1-tert-octyl-4-methyl-4-isothiobiuret hydrochloride, M.P. 187°–190° C.

8 Grams of the oil obtained above were dissolved in 30 ml of isopropyl alcohol and 3.2 g (2.2 ml) of 98% methanesulfonic acid was added dropwise with stirring and cooling. Precipitation was initiated by scratching the side of the flask. The precipitate was collected, washed with a mixture of isopropyl alcohol and diethyl ether, and recrystallized from isopropyl alcohol to yield 4.9 g of 1-tert-octyl-4-methyl-4-isothiobiuret methanesulfonic acid salt, M.P. 141°–144° C.

3 Grams (0.0106 mole) of 1-tert-octyl-4-methyl-4-isothiobiuret hydrochloride prepared above and 1.07 grams (0.0053 moles) of 1,4-bis(3-aminopropyl)piperazine were dissolved in 10 ml of methanol and allowed to stand overnight. The solution was treated with 150 ml of ether and refrigerated for 2 hours. A precipitate formed which was collected, triturated with ether, and dried to yield 3 g of a mixture 1,4-bis[3-(tert-octylcarbamylguanidino)propyl] piperazine di- and tri-hydrochlorides (found 2.2 moles of HCl), M.P. 135°–139° C., effervescence.

EXAMPLE III

This example illustrates the synthesis of 1,4-bis-3-(2-ethylhexyl)carbamylguanidino)propyl piperazine by the process of this invention.

15.3 Grams (0.07 mole) of S-methylisothiuronium iodide were dissolved in 75 ml of acetone containing 11 ml of triethylamine. 10.9 Grams (0.07 mole) of 2-ethylhexyl isocyanate dissolved in 10 ml of acetone were added dropwise and the mixture was allowed to stand for 2 hours. The precipitate which formed was removed by filtration and the filtrate, after treatment with 500 ml of water, yielded an oil. This was dissolved in cold isopropyl alcohol, and concentrated hydrochloric acid was added dropwise until the solution was acidic. Upon stirring and chilling a precipitate formed, which was collected, washed with isopropyl alcohol, and dried to yield 1-(2-ethylhexyl)-4-methyl-4-isothiobiuret hydrochloride. M.P. 128°–130° C.

Approximately 9.4 g of the oil prepared above were dissolved in 20 ml of isopropyl alcohol and 3.8 g of 98% methanesulfonic acid were added. The precipitate which formed was collected on a filter, washed with isopropyl alcohol and recrystallized from isopropyl alcohol to yield 1-(2-ethylhexyl)-4-methyl-4-isothiobiuret methanesulfonic acid salt. M.P. 112°–114° C.

1.5 Grams (0.0053 mole) of 1-(2-ethylhexyl)-4-methyl-4-isothiobiuret hydrochloride prepared above and 0.53 g (0.00266 mole) of 1,4-bis(3-aminopropyl)piperazine were dissolved in 3 ml of methanol and allowed to stand for several hours. The reaction mixture was then treated with about 150 ml of diethyl ether and refrigerated for 3 days. The ether was then decanted, fresh ether was added, and the precipitate was triturated until it solidified. The precipitate was then collected on a filter and dried to yield a mixture of 1,4-bis[3-{(2-ethylhexyl)-carbamyl-guanidino}propyl]piperazine di- and tri-hydrochloride salts, (found 2.2 moles of HCl). M.P. 85°–120° C.

EXAMPLE IV

This example illustrates the synthesis of 1,10-bis-(cyclohexanemethylcarbamylamidino)-1,4,7,10-tetramethyl-1,4,7,10-tetraazadecane.

3.19 Grams (0.012 mole) of 1-cyclohexanemethyl-4-methyl-4-isothiobiuret hydrochloride and 1.21 grams (0.006 mole) of 1,4,7,10-tetramethyltriethylenetetramine were dissolved in 10 ml of methanol and allowed to stand for 2 days. 200 Milliliters of diethyl ether were then added and the mixture was allowed to stand overnight in a refrigerator. The ether was decanted, and the residue was triturated with fresh diethyl ether, chilled until solid, collected on a filter, washed with diethyl ether and dried to yield a mixture of 1,10-bis(cyclohexanemethylcarbamylamidino)-1,4,7,10-tetramethyl-1,4,7,10-tetraazadecane di- and tri-hydrochlorides (found 2.5 moles of HCl), M.P. 100°–120° with effervescence.

EXAMPLE V

This example illustrates the synthesis of 1,6-bis-(cyclohexanemethylcarbamylguanidino)hexane by the process of this invention.

2.658 Grams (0.01 mole) of 1-cyclohexanemethyl-4-methyl-4-isothiobiuret hydrochloride prepared as in Example I, and 0.58 grams (0.005 mole) of 1,6-hexanediamine were dissolved in 8 ml of methanol and allowed to stand overnight. 300 Milliliters of diethyl ether were then added and the mixture was refrigerated. The gummy precipatate which formed was triturated with ether to yield a solid which was collected and dried to yield 1.7 g of a mixture of 1,6-bis(cyclohexanemethylcarbamylguanidino)hexane di- and trihydrochlorides (found 2.6 mole of HCl), M.P. Foams 120°–132° C., Melt 158° C.

3.25 Grams (0.01 mole) of 1-cyclohexanemethyl-4-methyl-4-isothiobiuret methanesulfonic acid salt and 0.58 g (0.005 mole) of 1,6-hexanediamine were suspended in 10 ml of methanol, stirred vigorously and allowed to stand for about 2 weeks. The precipitate was triturated with diethyl ether, collected by filtration and recrystallized from ethanol to yield 1,6-bis(cyclohexanemethylcarbamylguanidino)hexane dimethanesulfonic acid salt. M.P. sinters 110°–113° C., melts by 123° C.

EXAMPLE VI

This example illustrates the synthesis of 1,4-bis[2-(cyclohexanemethylcarbamylguanidino)ethyl] piperazine by the process of this invention.

6.5 Grams (0.02 mole) of 1-cyclohexanemethyl-4-methyl-4-isothiobiuret methanesulfonic acid salt and 1.7 g (0.01 mole) of 1,4-bis(2-aminoethyl)piperazine were mixed together in 10 ml of methanol and the resulting suspension was allowed to stand for one week. The precipitate was collected, triturated with cold methanol, again collected, washed with methanol, dried, and recrystallized from methanol to yield 3.6 g of 1,4-bis[2-(cyclohexanemethylcarbamylguanidino)ethyl]-piperazine dimethanesulfonic acid salt. M.P. 192°–193.5° C.

EXAMPLE VII

This example illustrates the synthesis of 1,4-bis[3-(hexylcarbamylguanidino)propyl]piperazine dimethanesulfonic acid salt by a preferred process of this invention.

136.6 g (0.626 mole) S-methylisothiourea hydroidide and 95 ml (69 g, 0.68 mole) triethylamine (excess not harmful) were combined in 525 ml of acetone. The solution was stirred and cooled in an ice bath. 79.7 g (0.626 mole) n-hexyl isocyanate were added. The ice bath was removed and the solution stirred for ca. 2 hr. The solution was poured onto ca. 2 l of ice-cold water and extracted with 3 portions of $CH_2Cl_2$. The combined $CH_2Cl_2$ fractions were washed with water and dried over anhydr. $K_2CO_3$. Filtration and evaporation yielded ca. 156.5 g of crude free 1-hexyl-4-methyl-4-isothiobiuret.

The above 156.5 g of isothiobiuret base were dissolved in 750 ml ethyl acetate, stirred mechanically and cooled in an ice bath. To this was slowly added ca. 60 g (0.63 mole) $CH_3SO_3H$ till the pH was clearly acidic (pH paper, pH<3). The resulting thick suspension was refrigerated for a few hours. The precipitate was then collected, washed with cold ethyl acetate and dried at room temperature in vacuo. Yield 182 g (93% of theory, based upon isocyanate), colorless solid, mp 128°–129° C.

Recrystallization from ca. 420 ml isopropyl alcohol afforded 167 g of white crystals of 1-hexyl-4-methyl-4-isothiobiuret methanesulfonic acid salt mp 129°–130.5° C. Overall yield, based upon isocyanate, 85%.

2.78 g (8.9 mmole) of this isothiobiuret acid addition salt, 0.3 g (1.44 mmole) of the isothiobiuret free base, and 0.9 g (4.8 mmole) 1,4-bis(3-aminopropyl)piperazine were combined in 5 ml isopropyl alcohol and refluxed for 2 hr. On cooling, seeding, scratching, and refrigeration the product crystallized out to give 2.56 g (73% of theory) of product, mp 108°–118° C.

Recrystallization from isopropyl alcohol (ca. 2 ml/g) proceeded in ca. 95% yield to give a ca. 63% overall yield of white solid, 1,4-bis[3-(hexylcarbamylguanidino)propyl] piperazine dimethanesulfonic acid salt mp 117°–120° C. (uncorr.), after drying in vacuo at 55° C.

I claim

1. A process for preparing bis(amidinoureas) of the formula

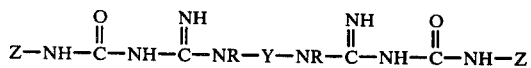

comprising reacting a 1-substituted-4-loweralkyl-isothiobiuret of the formula

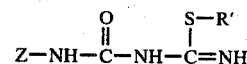

wherein Z is an aliphatic or alicyclic group and R' is a lower alkyl group, with a compound containing two aliphatic amino groups of the formula

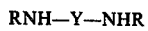

wherein R represents hydrogen or a lower alkyl group and Y is a divalent organic radical selected from the group consisting of
   (1) divalent straight and branched chain aliphatic radicals;
   (2) divalent alicyclic and non-aromatic heterocyclic radicals;
   (3) divalent carbocyclic aromatic and heterocyclic aromatic radicals having side chains; and
   (4) combinations of the above radicals linked directly or through hetero atoms selected from the group consisting of nitrogen, oxygen, or sulfur,
with the proviso that said Y group contains one or more nitrogen atoms and said isothiobiuret is used in the form of a mixture of the free base and an acid addition salt, the proportions of said free base and said addition salt being chosen so that the total amount of isothiobiuret is equal to or greater than the stoichiometric amount and the total amount of acid contained in the isothiobiuret salt is less than two moles per mole of compound containing two aliphatic amino groups.

2. A process according to claim 1 wherein said amount of isothiobiuret is greater than the stoichiometric amount.

3. A process according to claim 1 wherein said isothiobiuret free base is used in the proportion of 0.05 to 0.7 moles per mole of said compound containing two aliphatic amino groups.

4. A process according to claim 1 wherein said isothiobiuret acid addition salt is used in the proportion of 1.4 to 1.95 moles per mole of said compound containing two aliphatic amino groups.

5. A process according to claim 1 wherein said isothiobiuret free base is used in the proportion of 0.05 to 0.7 moles and said isothiobiuret acid addition salt is used in the proportion of 1.4 to 1.95 moles per mole of said compound containing two aliphatic amino groups.

6. A process according to claim 1 wherein said organic polar hydroxylic solvent has a dielectric constant greater than 18.

7. A process according to claim 1 wherein said organic polar hydroxylic solvent is methanol.

8. A process according to claim 1 wherein said organic polar hydroxylic solvent is ethanol.

9. A process according to claim 1 wherein said organic polar hydroxylic solvent is isopropyl alcohol.

10. A process according to claim 1 wherein said process is carried out at a temperature between 0° to 100° C.

11. A process according to claim 1 wherein said process is carried out at a temperature between 20° C. and 85° C.

12. A process according to claim 1 for the preparation of 1,4-bis[3-(hexylcarbamylguanidino)propyl]piperazine which comprises reacting 1,4-bis(3-aminopropyl)- piperazine with a mixture of 1-hexyl-4-methyl-4-isothiobiuret and an acid addition salt thereof.

13. A process according to claim 1 for the preparation of 1,4-bis[3-(hexylcarbamylguanidino)propyl]piperazine dimethanesulfonic acid salt which comprises reacting 1,4-bis(3-aminopropyl)piperazine with a mixture of 1-hexyl-4-methyl-4-isothiobiuret and 1-hexyl-4-methyl-4-isothiobiuret methanesulfonic acid salt.

* * * * *